United States Patent [19]

Cooper

[11] Patent Number: 4,602,116
[45] Date of Patent: Jul. 22, 1986

[54] PROCESS FOR THE SELECTIVE PRODUCTION OF KETONES

[75] Inventor: James L. Cooper, Longview, Tex.

[73] Assignee: Eastman Kodak Company, Rochester, N.Y.

[21] Appl. No.: 721,496

[22] Filed: Apr. 9, 1985

Related U.S. Application Data

[63] Continuation of Ser. No. 531,383, Sep. 12, 1983, abandoned.

[51] Int. Cl.$^4$ .................................................. C07C 45/49
[52] U.S. Cl. ....................................... 568/387; 568/451
[58] Field of Search ................................. 568/387, 451

[56] References Cited

U.S. PATENT DOCUMENTS 3,020,314 2/1962 Alderson ............................ 568/909
4,226,845 10/1980 Laine ................................. 568/882
4,306,084 12/1981 Pettit ................................. 568/451

FOREIGN PATENT DOCUMENTS 2545821 11/1984 France ............................... 568/387

OTHER PUBLICATIONS

Bianchi et al., Chem. Abst., vol. 49, #52808h (1983).
Laine, Chem. Abst., vol. 93, (#131768z), (1980).
Shultz et al., Ind. Eng. Chem. Prod. Res. Develop., vol. 12, p. 177, (1973).

Primary Examiner—James H. Reamer
Attorney, Agent, or Firm—Donald W. Spurrell; David E. Cotey; Daniel B. Reece, III

[57] ABSTRACT

The present invention provides a process for the selective production of ketones under hydroformylation conditions. In particular, the process comprises the hydroformylation of at least one olefin in the presence of hydrogen, carbon monoxide, and a catalyst which consists essentially of triruthenium dodecacarbonyl. The olefin preferably comprises propylene. The reaction is conducted under conditions such that the ratio of olefin:ruthenium is about 200:1 to 3000:1, the ratio of carbon monoxide:hydrogen:olefin to about 1:1.4:4 to 1:6:100, the total pressure is about 500 to 10,000 psig, the carbon monoxide partial pressure is about 50 to 500 psig, and the reaction temperature is about 60° to 250° C.

6 Claims, No Drawings

PROCESS FOR THE SELECTIVE PRODUCTION OF KETONES

This is a continuation of application Ser. No. 531,383 filed Sept. 12, 1983, now abandoned.

DESCRIPTION

The present invention relates to the preparation of oxygenated organic compounds by the reaction of carbon monoxide and hydrogen with an olefinic compound in the presence of a transition metal catalyst. More specifically, the invention relates to a highly active ruthenium catalyst which provides the capability to produce ketones.

It is known in the art that oxygenated organic compounds can be synthesized from olefins by the reaction of carbon monoxide and hydrogen in the presence of homogeneous catalyst systems under limited conditions known as Oxo or hydroformylation conditions. It is further known in the art that by-products such as alcohols, formate esters, ketones, and aldol-type products are obtained. Heretofore, considerable emphasis has been placed on the production of aldehydes by Oxo processes and, more particularly, on the production of relatively high ratios of normal to branched aldehyde products. See, for example, U.S. Pat. Nos. 3,527,809, 3,917,661, 3,965,192, and 4,148,830. For such processes, the catalyst is typically cobalt or rhodium complexed with such materials as carbonyl, phosphines, and phosphites.

It is known that dialkyl ketones can be produced by the hydrocarbonylation of olefins by means of a transition metal catalyst. The yield of ketone has been shown to be strongly dependent upon the olefinic structure, and only ethylene has given rise to a ketonic product in substantial yield. It is disclosed by Murata et al, Chem. Lett., 1980, p. 11, that good selectivities to dipropyl ketones can be achieved with a catalyst system prepared in situ from dicobalt octacarbonyl and 1,2-bis(diphenylphosphino)ethane under a carbon monoxide atmosphere in the presence of water. A major disadvantage of this type of system is the high cost of the chelating phosphine ligands.

Shultz et al, Ind. Eng. Chem. Prod. Res. Develop., 12, 177 (1973), teaches that ruthenium oxide ($RuO_2$ aq) and ruthenium trichloride ($RuCl_3$ aq), can be used in the hydroformylation of propylene at a hydrogen to carbon monoxide ratio of 2:1 and reaction conditions of 4500 psig and 90° to 150° C. Butyraldehydes and butanols are the major products of the reaction. However, a small quantity of heptanones were observed as by-products.

The present invention, in contrast to the prior art, provides a process by which ketones can be produced in excellent yield under specified reaction conditions using a ruthenium catalyst. The process of the present invention is especially useful for the production of ketones from propylene in excellent yields.

SUMMARY OF THE INVENTION

The present invention provides a process for the production of ketones by the hydroformylation of at least one olefin in the presence of hydrogen, carbon monoxide, and a catalyst consisting essentially of triruthenium dodecacarbonyl. The ratio of olefin:ruthenium is about 200:1 to 3000:1, the ratio of carbon monoxide:hydrogen:olefin is about 1:1.4:4 to 1:6:100, the total pressure is about 500 to 10,000 psig, the carbon monoxide partial pressure is about 50 to 500 psig, and the reaction temperature is about 60° to 250° C.

DETAILED DESCRIPTION OF THE INVENTION

The present invention provides a hydroformylation process by which ketones can be selectively produced in good yield. More specifically, the present invention utilizes a ruthenium catalyst to synthesize dialkyl ketones from olefin, carbon monoxide, and hydrogen. According to the present invention, a high selectivity to ketone is achieved under a specific set of reaction conditions.

In accordance with the process of the present invention, at least one olefin is contacted with carbon monoxide and hydrogen under hydroformylation conditions. The olefin which may be employed in the process of the present invention can be any ethylenically unsaturated compound. Especially suitable compounds include ethylene, propylene, butene-1 and higher molecular weight alpha-olefins. Preferred feedstocks for the process of the present invention comprise ethylene and propylene.

The carbon monoxide and hydrogen reactants which are employed in the process of the present invention are preferably provided as a mixture, e.g., in the form of synthesis gas. Synthesis gas can be prepared from a wide range of hydrocarbon raw materials including natural gas, petroleum and petroleum residues, coal, etc., by well-known methods such as steam reforming, partial oxidation, coal gasification, etc.

The relative amounts of hydrogen and carbon monoxide which are present in the reaction mixture must be carefully controlled in order to achieve the object of the present invention, i.e., the production of ketones. In addition, the amount of olefin which is present in relation to the amount of hydrogen and carbon monoxide which is present must also be carefully controlled. In particular, it is necessary that the molar ratio of carbon monoxide:hydrogen:olefin be maintained between about 1:1.4:4 and 1:6:100.

In addition to carefully controlling the relative amounts of these reactants, it is necessary to maintain the total amounts of gaseous reactants employed within certain limits. Thus, in accordance with the present invention, it is desirable to maintain the total reaction pressure between about 500 to 10,000 psig. Preferably, a pressure of about 1000 to 2500 psig is employed. Within these limitations on the total reaction pressure, the partial pressure of carbon monoxide must be greater than about 50 psig but less than about 500 psig.

Also present in the reaction system of the process of the present invention is a catalyst which consists essentially of triruthenium dodecacarbonyl. A wide range of catalyst concentrations may be used. Concentrations as high as 1% by weight of ruthenium per volume of solvent may be used, but concentrations below 1 ppm may also be used to advantage. Preferably, the ruthenium is present in a concentration between about 500 and 5000 ppm. Within these limitations on the total amount of ruthenium present in the system, it is also necessary to correlate the relative amounts of olefin and catalyst which are present. In particular, it is desirable to maintain a high molar ratio of olefin to ruthenium. Thus, a molar ratio of olefin to ruthenium of about 200:1 to 3000:1 is preferably maintained for good ketone selectivity.

The catalyst may be charged to the reaction vessel in any soluble form which provides the active catalyst species, i.e., triruthenium dodecacarbonyl. This species can be obtained by the carbonylation under reaction conditions of such compounds as ruthenium dioxide, ruthenium trichloride, etc., as is well known in the art. However, it is preferred procedure to prepare the triruthenium dodecacarbonyl catalyst beforehand and introduce it to the reaction system in that form.

The reaction system further comprises a solvent which does not adversely affect the process and which is inert with respect to the catalyst, olefin, synthesis gas, and the hydroformylation products. Such solvents may include saturated and unsaturated hydrocarbons, alcohols, ethers, esters, and carboxylic acids. Specific examples of suitable solvents include hexane, decane, benzene, toluene, ethanol, hexanol, diethyl ether, glyme, diethylene glycol, acetic acid, butyric acid, and mixtures thereof. Acetic acid is a preferred solvent.

The hydroformylation reaction is conducted under standard temperature conditions. For example, the reaction is preferably conducted at a temperature of about 60° to 250° C., and, preferably, at a temperature of about 100° to 175° C.

The hydroformylation process can be conducted for any period of time which is sufficient to provide products in a desirable yield. Generally, a reaction period of about 0.25 to 20 hours is suitable. Preferably, the hydroformylation reaction is conducted for a period of time of about 2 to 10 hours.

In carrying out the hydroformylation process in a continuous manner, conventional Oxo process equipment and procedures may be employed. For example, the reaction zone may comprise an overflow reactor with the catalyst leaving the reaction zone together with the product mixture. The product mixture can then be passed through a series of vapor/liquid separators with the gases being recycled to the reactor and the liquid being let down to atmospheric pressure by conventional techniques. The liquid product mixture comprises ketone products, aldehyde by-products, solvent, and catalyst. This liquid product stream can be passed through a distillation column to remove products overhead and the catalyst, together with high boiling effluent, being recycled back to the reactor through suitable pumping means. The product taken overhead can then be separated by further processing.

By means of the above-described novel process, ketones are selectively produced from olefins and synthesis gas using a specified ruthenium catalyst. The catalyst of the present invention is less complex and less expensive than the prior art catalysts which required expensive complexing agents such as triphenylphosphine, 1,2-bis(diphenylphosphino)ethane, halogen, and/or amines such as pyridine and benzoamine. Furthermore, the process of the present invention employs relatively low reaction temperatures and pressures and achieves high production rates and high selectivity for ketone formation. The ketones which are produced by means of the process of the present invention are well known in the art as useful solvents in coating compositions and other applications.

The present invention is illustrated further by the following Examples although it will be understood that these Examples are included merely for purposes of illustration and are not intended to limit the scope of the invention.

EXAMPLE 1

This Example illustrates the preparation of a mixture of heptanones from propylene under the conditions of the present invention.

Triruthenium dodecacarbonyl (2.0 grams) was combined with 100 ml of toluene in a 300-ml stainless steel autoclave equipped with a stirrer and automatic cooling. After chilling the autoclave in dry ice, propylene (90 grams, propylene:ruthenium molar ratio=214:1) was charged into the autoclave. Synthesis gas having a hydrogen to carbon monoxide molar ratio of 2:1 was then introduced into the reactor at a pressure of 1000 psig. The temperature was raised to 100° C., with the pressure increasing to 1450 psig. The reaction pressure was then further increased to 1500 psig and maintained at this level for the duration of the 9.5 hour run. The system was then cooled and vented. A weight gain in liquid product of 16.15 grams was recorded. The composition of the product mixture was determined by gas-liquid chromatography and mass spectral analysis. The selectivity to ketone products was 22.9 percent with a ratio of hepta-4-one to 2-methylhexa-3-one of 1.67:1 being observed. The balance of the product mixture was butyraldehydes. Butanols were not observed in the product.

It can be seen that under conditions taught by the present invention (specifically, a carbon monoxide:hydrogen:propylene ratio of 1:2:10.4) ketone products can be selectively produced from propylene.

EXAMPLE 2

The procedure of Example 1 was repeated except that the triruthenium dodecacarbonyl catalyst was charged in an amount of 0.4 grams, the propylene charge was 40 grams (propylene:ruthenium ratio of 534:1), the hydrogen to carbon monoxide molar ratio was 3:1, and the reaction time was 9.5 hours. The $CO:H_2$:propylene ratio was 1:3:6.7. A weight gain of 23.5 grams was recorded. Analysis of the product showed a 43% selectivity to ketones with a hepta-4-one to 2-methylhexa-3-one ratio of 1.7:1.

EXAMPLE 3

The procedure of Example 1 was repeated except that the triruthenium dodecacarbonyl catalyst charge was 0.1 grams, the propylene charge was 40 grams, the reaction solvent was acetic acid, the hydrogen to carbon monoxide molar ratio was 1.4:1, and the 2-hour reaction was conducted at 150° C. and 1000 psig. The carbon monoxide:hydrogen:propylene ratio was 1:1.4:5.52. A weight gain of 44.5 grams was recorded and the product rate was 13.9 pounds per cubic foot-hour. The selectivity to ketone products was 38% with a ratio of hepta-4-one to 2-methylhexa-3-one of 1.57:1.

EXAMPLE 4

The procedure of Example 1 was repeated except that the triruthenium dodecacarbonyl catalyst charge was 0.4 gram, the molar ratio of hydrogen to carbon monoxide was 3:1, the reaction solvent was acetic acid, and the reaction time was 2.5 hours. The carbon monoxide:hydrogen:propylene ratio was 1:3:12.8. A weight gain of 17.1 grams was recorded. Analysis of the liquid product showed a 50% selectivity to ketone products with a ratio of hepta-4-one to 2-methylhexa-3-one of 1.48:1.

EXAMPLE 5

The procedure of Example 4 was repeated except that the reaction temperature was 150° C. and the reaction time was 2 hours. A weight gain of 32.4 grams was recorded. Analysis of the liquid product showed a 52% selectivity to ketone with a ratio of hepta-4-one to 2-methylhexa-3-one of 1.42:1.

EXAMPLE 6

The procedure of Example 4 was repeated except that the reaction temperature was 150° C. and the molar ratio of hydrogen to carbon monoxide was 5.2:1. The ratio of carbon monoxide:hydrogen:propylene was 1:5.2:10.7. A weight gain of 24.4 grams was recorded. Analysis of the liquid product showed a ketone selectivity of 51% and a ratio of hepta-4-one to 2-methylhexa-3-one of 1.51:1.

EXAMPLE 7

Triruthenium docecacarbonyl (0.4 grams) was combined with 100 ml of glacial acetic acid in a 300 ml stainless steel autoclave equipped with a stirrer and automatic cooling. Ethylene (600 psig) and 300 psig of synthesis gas ($H_2$:CO molar ratio of 3:1; carbon monoxide:hydrogen:ethylene molar ratio of 1:3:5.9) was then introduced into the reactor and the temperature was raised to 150° C. with the pressure increasing to 1300 psig. The reaction pressure was increased further to 1500 psig and was maintained at this level for the duration of the 17-minute run. The system was then cooled and vented. A weight gain of 20.1 grams was recorded. The composition of the product mixture was found to be diethyl ketone (51.7%) and propionaldehyde (48.3%).

COMPARATIVE EXAMPLE 1

This Comparative Example illustrates the preparation of a mixture of heptanones from propylene using ruthenium isobutyrate as a catalyst. The results are far less advantageous than those obtained using the catalyst of the process of the present invention.

Ruthenium isobutyrate (2.0 grams) was combined with 100 ml of toluene in a 300-ml stainless steel autoclave equipped with a stirrer and automatic cooling. After chilling the autoclave in dry ice, propylene (80 grams) was charged into the autoclave. Synthesis gas having a hydrogen:carbon monoxide ratio of 2:1 was then charged to the autoclave until a pressure of 1200 psig was attained. The temperature was raised to 100° C., and the pressure was increased to 1500 psig. This pressure was maintained throughout the 9.5 hour period of reaction. The system was then cooled and vented. A weight gain in liquid product of 18.1 grams was recorded. The composition of the product mixture was determined by gas-liquid chromatography and mass spectral analysis. The selectivity to ketone products was 8.7% with a ratio of hepta-4-one to 2-methylhexa-3-one of 1.6:1. The balance of the product mixture comprised butyraldehydes.

COMPARATIVE EXAMPLE 2

This Comparative Example illustrates the undesirable results achieved by a hydroformylation process which employs conditions other than those taught by the present invention.

Triruthenium dodecacarbonyl (2.0 grams) was combined with 100 ml of toluene in a 300-ml stainless steel autoclave equipped with a stirrer and automatic cooling. After chilling the autoclave in dry ice, propylene (90 grams) was charged into the autoclave. Synthesis gas having a hydrogen to carbon monoxide molar ratio of 1:2 was introduced into the reactor until a pressure of 1000 psig was obtained. The temperature was raised to 120° C., and the pressure was increased to 1400 psig. The reaction pressure was further increased to 1500 psig and was maintained at this level for the duration of the 9.5 hour run. The system was then cooled and vented. A weight gain in liquid products of 9.4 grams was recorded. The composition of the product mixture was determined by gas-liquid chromatography and by mass spectral analysis. The selectivity to ketone products was 1.3% with a ratio of hepta-4-one to 2-methylhexa-3-one of 1.8:1 being observed. The balance of the product mixture was butyraldehydes.

It can be seen that an extremely poor selectivity to ketone products was obtained at the molar ratio of carbon monoxide:hydrogen:propylene of 1:0.5:5, which ratio falls outside the reaction conditions of the present invention.

The invention has been described in detail with particular reference to preferred embodiments thereof, but it will be understood that variations and modifications can be effected within the spirit and scope of the invention.

I claim:

1. A process for the production of ketones by the hydroformylation of at least one olefin in the presence of hydrogen, carbon monoxide, and a catalyst consisting essentially of triruthenium dodecacarbonyl wherein the molar ratio of olefin:ruthenium is about 200:1 to 3,000:1, the moler ratio of carbon monoxide:hydrogen:olefin is about 1:1.4:4 to 1:6:100, the total pressure is about 500 to 10,000 psig, the carbon monoxide partial pressure is about 50 to 500 psig, and the reaction temperature is about 60° to 250° C.

2. The process of claim 1 wherein said olefin comprises propylene.

3. The process of claim 1 wherein the total pressure is about 1,000 to 2,500 psig.

4. The process of claim 1 wherein the reaction temperature is about 100° to 175° C.

5. The process of claim 1 wherein said hydroformylation reaction is conducted for a period of time of about 0.25 to 20 hours.

6. The process of claim 5 wherein said hydroformylation reaction is conducted for a period of time of about 2 to 10 hours.

* * * * *